United States Patent [19]

Cavalcante

[11] 4,441,610

[45] Apr. 10, 1984

[54] CONTAINER FOR THE STORAGE AND WITHDRAWAL OF EAR CLEANING STICKS OR SIMILAR ARTICLES

[75] Inventor: Mario Cavalcante, Thiene, Italy

[73] Assignee: Ivalda S.p.A., Italy

[21] Appl. No.: 264,327

[22] Filed: May 18, 1981

[30] Foreign Application Priority Data

May 16, 1980 [IT] Italy ............................ 64254/80[U]

[51] Int. Cl.³ .............................................. B65D 8/00
[52] U.S. Cl. ..................................... 206/361; 206/37; 206/261; 220/334; 220/337
[58] Field of Search ................. 206/37, 261, 263, 265, 206/256, 815, 361; 248/205 A; 220/334, 337

[56] References Cited

U.S. PATENT DOCUMENTS

| 759,578 | 5/1904 | Williams | 206/121 |
|---|---|---|---|
| 829,598 | 8/1906 | Ohl | 206/121 |
| 1,989,159 | 1/1935 | Shiffman et al. | 220/334 |
| 2,883,853 | 4/1959 | Forni | 220/334 |
| 2,905,356 | 9/1959 | Jerome | 220/337 |
| 3,261,126 | 7/1966 | Marks | 248/205 A |
| 3,655,119 | 4/1972 | Thompson | 206/37 |

FOREIGN PATENT DOCUMENTS

| 2906098 | 2/1979 | Fed. Rep. of Germany | 206/37 |
|---|---|---|---|
| 543632 | 9/1922 | France | 206/261 |
| 607617 | 6/1926 | France | 206/261 |
| 20341 | of 1901 | United Kingdom | 206/261 |
| 2048218 | 12/1980 | United Kingdom | 206/362 |

OTHER PUBLICATIONS

Modern Packaging, "Plastic Drill Cases", Jul. 1947 p. 115.

Primary Examiner—George E. Lowrance
Assistant Examiner—Jimmy G. Foster
Attorney, Agent, or Firm—Allison C. Collard; Thomas M. Galgano

[57] ABSTRACT

A container for the facile storage and withdrawal of ear-cleaning sticks or similar articles includes two shell bodies, at least one of which is pivotable relative to the other for movement between an open and closed position or in the former of which it exposes a stick reservoir. The container is closed by a light snap action. The container has a generally tubular shape and has two flat end faces. Both shells may be provided by a single molding operation of thermoplastic material.

5 Claims, 3 Drawing Figures

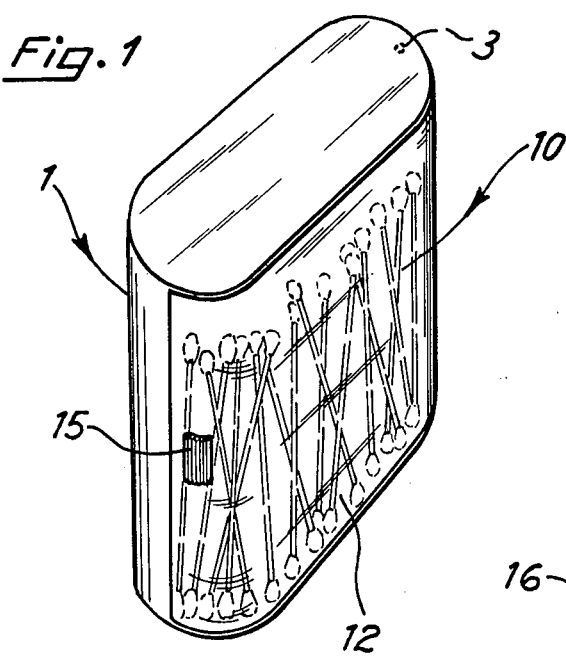
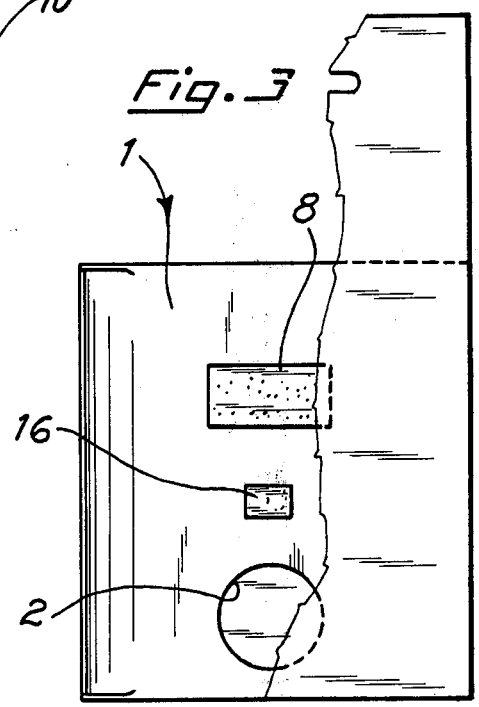
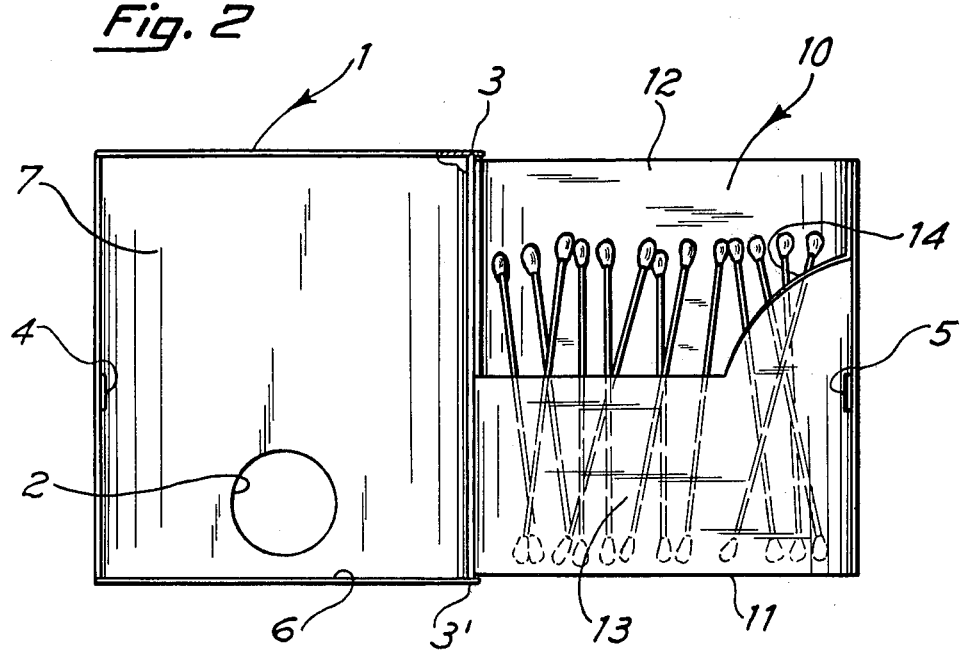

CONTAINER FOR THE STORAGE AND WITHDRAWAL OF EAR CLEANING STICKS OR SIMILAR ARTICLES

The present invention relates to a container particularly suitable for the storage and withdrawal of ear cleaning, cotton covered sticks or similar objects used for cosmetic and hygienic care.

In common hygiene everyday and particularly in the care of children, small plastic sticks having a firmly secured flock of cotton wrapped about the ends thereof are used.

With the two heads thus formed, either medicated or not, may enable a very good hygiene at delicate or localized or hardly accesible zones, particularly for cleaning and treatment of the auricular canals of one's ears. Owing to this specific use it is disadvantageous to leave them in various small packets or in containers of difficult access. Consequently, small transparent tubular containers having an external fit cap are typically used, the caps of which are sometimes provided with holes for the removal of the sticks. Moreover, such cases or containers should be made more readily available in the proximity of a washbasin, or on a child's care table or at a dressing table.

Further, it should be considered that the lightness of the sticks and of the conventional containers or cases makes their positioning very unstable so that they may easily fall or overturn.

The present invention achieves all of the aforesaid useful objects and avoids the disadvantages of the hitherto used approaches.

In the drawing:

FIG. 1 is a perspective view of a container embodying the present invention, further showing in phantom line the storage therein of a multiplicity of ear-cleaning sticks;

FIG. 2 is a front elevational view with the container shown in an open position; and FIG. 3 is a rear elevational view of the container shown in a closed position.

As clearly shown in the figures a container is provided which comprises a base body 1, generally made of opaque thermoplastic material, of flattened tubular shape with a missing front wall, so that it includes a rear flat wall ending at its sides with two curved surfaces. The rear wall is provided with a control hole 2. Base body 1 is completed by two preferably flat end surfaces which determines the height of the body and, in turn, the container; at one end of each of the two flat surfaces are positioned two holes, blind or through holes, in which holes two prongs or nibs 3 and 3' will engage owing to a light resilient bending, such prongs or nibs being secured on a second body 10.

At the middle of the end line of the other lateral curved surface, said base body is provided via a molding operation a with small lug 4 for coupling with the complementary lug 5 on second body 10.

Said second body 10 is the movable part of the container and comprises a single bottom 11 which forms with the bottom of the stick reservoir or case and profile for exact insertion on the bottom flat surface 6 of body 1. The stick reservoir or case is contained within a cavity delimited by two walls, namely a semitubular wall 12 corresponding to the missing part of the base body 1, and a second wall 13 having a height reduced to about one half and a slightly reduced external size relative to the internal size of the stationary semitubular wall 7. This movable part 10, generally molded of transparent plastic material, carries on its end line or edge of its lateral curved wall, a ridge along its entire length; side ridge projecting by a few millimeters in both directions beyond the height of said lateral curved wall to form said two prongs or nibs 3 and 3'. It should be further noted that the stick reservoir or case would improve its features of ordered containment should the semitubular wall 13 have an inclined edge length or section 14 which, from beyond the center line of the flat part moves up for about one fourth of the semitube height on the hinge side.

Thus, by molding only two pieces, a casket-like container is provided which is of very high stability in the horizontal position, which is kept fully closed by means of lugs 4 and 5.

To use the container, it should be vertically placed and, through the hole 2 of the base body 1, a push action is exerted on the part 13, and thereby the entire body 10 rotates about prongs 3, 3' to provide easy access to the stick reservoir or case, so that the easiest sticks to be gripped are those gradually moving down along the inclined edge 14. The particular configuration makes the device steady even in the vertical open position.

In an alternate embodiment of the invention, when it is desired to hang or suspend the container, for example, secured to the bathroom wall it, is provided with a self-adhesive small strip or stripe 8 which, as shown in FIG. 3, is placed on the rear face of the base body 1. Such a self-adhesive double faced strip or stripe adheres by one face to the container body at the time of manufacture, whereas the second face, following removal of a release strip or anti-adhesive sheet, will be secured to the suitably degreased bathroom wall.

In this case, since the hole 2 is no longer available, for opening the container, the user must apply pressure on the small ridges 15 projecting from body 10, or by exerting a slight nail pressure along the corresponding free ends of front wall of body 10 and the rear wall of body 1.

For better retail display, the container carries on its rear side a small self-adhesive member by which it may be attached to a display board supporting it, which is typical for wide distribution.

If the container is fixed to a wall, the self-adhesive member 16 is left in its place after removal from the display board, but if, on the other hand, it is not to be fixed to a wall, it should be removed.

The container may be provided on the outer front wall of the movable body 10 with a relief trademark, which may be colored or not.

Besides, to prevent the unwanted opening of the container before its sale, and to insure the integrity of the packaging, a small self-adhesive stripe is attached (not shown) when the container is in the closed position to both the end sides opposite to the hinge of the container's walls.

What is claimed is:

1. A container for the storage and removal of hygienic cleaning sticks, comprising:
   a first body and a second body pivotably connected to said first body so that it is movable relative thereto between an open and closed position, in the latter position of which said bodies cooperate to define a single flattened tubular body, with two flat front and rear walls connected by two generally semicylindrical side walls and two generally flat top and bottom walls, which top and bottom walls are integral with said first body and are disposed at a right angle to said front and rear walls, said first body comprising said rear wall which is further provided with a finger hole formed therethrough and two curved lateral end walls joined to opposite lateral edges of said rear wall and said top and bottom walls integrally joined to said rear walls and said lateral end walls, and said second body comprising said front wall, two additional curved lateral end walls joined to opposite lateral edges of said front wall, a base wall joined to the lower edge of said front wall and said additional curved lateral end walls and disposed in a generally normal manner relative thereto, and an inner wall spaced rearwardly of said front wall and joined to said base wall and said additional curved lateral end walls, which is about one half the height of said front and rear walls and is dimensioned and configured to complement the inner profile of said first body such that it lies flush against at least a portion of the inner surface of said rear wall of said first body when said bodies are in said closed position thereof, said inner, base, front and additional curved lateral end walls of said second body cooperating to form a storage compartment for said hygienic cleaning sticks wherein the top of said compartment is open when said first and second bodies are in the open position, said second body being secured by a hinge to said first body for pivotable movement along a free edge of one of said additional curved lateral end walls thereof, said hinge comprising a pair of cooperating nibs and holes, said nibs being mounted on one of said bodies and said holes being formed in the other of said bodies, said pivotable movement permitting said first and second bodies to be moved to a closed position by telescoping said second body into said first body wherein said base wall of said second body is nested upon the bottom wall of said first body and said top wall of said first body closes the top of said storage compartment, said inner wall having a section slanting up for about one fourth of the container height towards a lateral side edge of said front wall distal to said hinge, said inner wall and said slanting section cooperating to contain said hygienic cleaning sticks within said compartment when said first and second bodies are in the open position, said bodies being releasably maintained in said closed position by two cooperating lugs, one of which is provided on a free edge of the curved lateral end wall of said first body distal from said hinge and the other of which is provided on a free edge of the curved lateral end wall of said second body distal from said hinge, said second body having generally in the middle of the external surface of said curved lateral end wall thereof distal from said hinge, a small narrow finger-engageable ridge to facilitate opening of the container.

2. The container of claim 1, wherein one of said holes is formed in said top wall and the other of said holes is formed in said bottom wall and wherein said nibs are provided on opposite ends of said free edge of said additional curved lateral end wall of said second body about which it is pivotable.

3. The container of claim 1, wherein said rear wall of said first body has secured thereto a self-adhesive strip protected by an anti-adhesive sheet, the removal of which allows the container to be attached to a wall.

4. The container of claim 3, additionally including a second self-adhesive strip secured to the rear wall of said first body for securing said container to a display board.

5. The container of claim 1, wherein said bodies are made from thermoplastic material.

* * * * *